United States Patent
Jorgensen (10) Patent No.: US 7,868,774 B2
(45) Date of Patent: Jan. 11, 2011

(54) OIL LEAKAGE DETECTOR

(75) Inventor: Torben Jorgensen, Herlev (DK)

(73) Assignee: Daspos A/S (DK)

( * ) Notice: Subject to any disclaimer, the term of this patent is extended or adjusted under 35 U.S.C. 154(b) by 261 days.

(21) Appl. No.: 12/297,782

(22) PCT Filed: Apr. 20, 2007

(86) PCT No.: PCT/DK2007/000190

§ 371 (c)(1), (2), (4) Date: Oct. 20, 2008

(87) PCT Pub. No.: WO2007/121750

PCT Pub. Date: Nov. 1, 2007

(65) Prior Publication Data

US 2009/0096618 A1    Apr. 16, 2009

Related U.S. Application Data

(60) Provisional application No. 60/793,727, filed on Apr. 21, 2006.

(30) Foreign Application Priority Data

Apr. 21, 2006   (EP) .................................. 06008277

(51) Int. Cl.
  *G08B 21/00* (2006.01)
  *G08B 17/10* (2006.01)
  *G01F 25/00* (2006.01)
  *G01L 27/00* (2006.01)
  *G01N 30/02* (2006.01)
  *G01N 11/08* (2006.01)

(52) U.S. Cl. .................. 340/606; 340/607; 340/611; 340/618; 340/608; 340/632; 73/1.35; 73/1.57; 73/1.71; 73/19.02; 73/54.06

(58) Field of Classification Search .................. 340/605
See application file for complete search history.

(56) References Cited

U.S. PATENT DOCUMENTS 3,696,666 A    10/1972   Johnson et al.

(Continued)

FOREIGN PATENT DOCUMENTS

DE    4407969 A1    9/1994

(Continued)

OTHER PUBLICATIONS

International Search Report filed in International Application No. PCT/DK2007/000190.

(Continued)

*Primary Examiner*—Daniel Wu
*Assistant Examiner*—Pameshanand Mahase
(74) *Attorney, Agent, or Firm*—Brooks Kushman P.C.

(57) ABSTRACT

An oil leakage detector for detecting the leakage of e.g. diesel or fuel oil in an engine room of a vessel comprises a conduit for an airflow therethrough, and a screen in the conduit. The screen is meshed to prevent oil particles or droplets from passing therethrough. A sensor determines a pressure loss across the screen, and a control system operatively connected to the sensor is configured to output an oil leakage warning signal if the pressure loss exceeds a predetermined threshold value. A fan may be provided for generating the airflow through the conduit. A gas sensor for determining the presence of hydrocarbon, carbon monoxide or carbon dioxide is optionally provided.

11 Claims, 6 Drawing Sheets

U.S. PATENT DOCUMENTS

| | | | |
|---|---|---|---|
| 4,263,805 A | | 4/1981 | Isley et al. |
| 4,515,690 A | * | 5/1985 | Yasuhara ..................... 210/90 |
| 4,701,621 A | * | 10/1987 | Kaiser et al. ................ 250/435 |
| 4,751,501 A | * | 6/1988 | Gut ............................ 340/607 |
| 5,602,373 A | | 2/1997 | Sauer et al. |
| 5,932,795 A | | 8/1999 | Koutrakis et al. |
| 2005/0154495 A1 | * | 7/2005 | Shah .......................... 700/276 |
| 2005/0178272 A1 | * | 8/2005 | Kariya et al. ................ 96/421 |
| 2005/0203493 A1 | * | 9/2005 | Kuroda et al. ................ 606/5 |

FOREIGN PATENT DOCUMENTS

WO          9841858 A2     9/1998

OTHER PUBLICATIONS

Quaglia G. et al.: Innovative device and process for the oil leakage measure Industrial Technology, 2003 IEEE International Conference on Maribor, Slovenia, Dec. 10-12, 2003, Piscataway, NJ, USA, IEEE, vol. 1, Dec. 10, 2003, pp. 129-134, ISBN: 0-7803-7852-07. US 5 932 795.

* cited by examiner

OIL LEAKAGE DETECTOR

CROSS-REFERENCE TO RELATED APPLICATION

This application claims the benefit of U.S. provisional application Ser. No. 60/793,727 filed Apr. 21 2006.

TECHNICAL FIELD

The present invention relates to an oil leakage detector, in particular for detecting the presence of fuel, diesel or hydraulic oil in an engine room of a vessel. The invention also relates to a vessel including such an oil leakage detector.

BACKGROUND OF THE INVENTION

Oil leaking out of e.g. a high pressure conduit for the supply of fuel in a vessel is hazardous due to the risk of fire and/or explosion. Moreover, if an oil leakage in an engine room is discovered late, the leaked oil will cover all surfaces in the engine room and leave an immense cleaning task for the crew. For these reasons it is desirable to detect an oil leakage as early as possible.

Various oil leakage detectors are known from the prior art. Most commercially available detectors rely either on a gas sensor for detecting the presence of e.g. carbon dioxide in air or on an optical system, in which light reflected from oil particles or droplets is detected. Systems relying solely on gas sensors have been found to be unreliable in many instances. Whereas systems relying on optics and light for detecting the presence of oil have become popular, they suffer from the drawback that they react too slowly in case an oil leakage produces relatively large droplets of oil, as they do not emit a warning signal until the density of oil exceeds the acceptable threshold value by far. This is believed to be due to the fact that large oil particles or droplets provide a relatively small reflection per unit weight in comparison to smaller particles, which provide a higher reflection per unit weight. Accordingly, there is a need for an oil leakage detector which is reliable, and which emits the appropriate warning signal even in the case of large oil particles or droplets.

SUMMARY OF THE INVENTION

It is therefore an object of preferred embodiments of the present invention to provide an oil leakage detector, which solves the above problems.

The invention provides an oil leakage detector, comprising:
 a conduit for an airflow therethrough;
 a screen in the conduit, the screen being meshed to at least partially prevent oil particles or droplets from passing therethrough;
 a sensor for determining a pressure loss across the screen;
 a control system operatively connected to the sensor, the control system being configured to output a warning signal if the pressure loss exceeds a predetermined first threshold value.

It will thus be appreciated that the present detector neither relies solely on gas detection nor solely on optical detection of light reflection, but rather on a pressure measurement. Thanks to the provision of a screen and a pressure sensor for detecting the pressure loss across the screen, drawbacks related to light reflection are overcome. Tests have shown that the present invention detects relatively large as well as relatively small oil particles in a reliable manner.

A fan is preferably provided for generating the airflow through the conduit. For a typical vessel application, the fan may be adapted to generate an airflow of 500-1500 $m^3$ per hour. In one embodiment, the fan provides approximately 900 $m^3$ per hour. Preferably, the oil leakage detector is dimensioned to be arranged in the engine room of a vessel. It may e.g. be mounted to a wall, floor or ceiling surface in an engine room and comprise means for its mounting at such a location. Several detectors may be connected to a common control panel.

The conduit may inexpensively be formed by a standard vent pipe, which is perforated to allow air to be drawn into the pipe. Preferably, the screen is arranged at a downstream location In the conduit. The fan may be arranged upstream or downstream of the screen. In a preferred embodiment, the fan is arranged downstream of the screen.

For additional security, a gas sensor may be provided for determining the presence of at least one gas in the airflow in the conduit. The gas sensor may e.g. be for the detection of hydrocarbon, carbon monoxide and/or carbon dioxide. In one embodiment, the gas sensor causes the control system to output a warning signal if the concentration of one of the aforementioned gases exceeds a predetermined concentration threshold value, in particular if the concentration of hydrocarbon and/or carbon monoxide exceeds a carbon monoxide concentration threshold value.

In order to provide a warning if there is an error in electrical parts of the control system, sensors or power supply, a signal may be emitted e.g. if the gas sensor output current drops below a predetermined value, such as below 4 mA. Likewise, a signal may be emitted if the electrical output of the pressure sensor drops below a predetermined value, corresponding e.g. to a pressure drop below 80-120 Pa, such as below 100 Pa.

For convenient control, the control system may be connected to the gas sensor. In a preferred embodiment, the control system is configured to emit an error signal and/or a warning signal in one or more of the following events:
 the pressure loss exceeds a predetermined threshold value due to oily atmosphere;
 fan failure;
 clogged screen;
 gas sensor failure.

In order to determine the difference between a clogged screen and the presence of an oil leakage, the control system is preferably adapted to monitor the pressure loss across the screen over time, i.e. continuously. A relatively sudden and significant increase of pressure loss within, e.g. minutes or a few hours, indicates the presence of oil in the air drawn through the conduit and thus an oil leakage. In contrast, a slow increase of pressure loss over e.g. several days to a pressure loss above a certain limit, indicates that the screen has become clogged.

In one embodiment, the pressure loss across the screen is 100-170 Pa under normal conditions (no oil leakage). In the case of a relatively sudden increase of pressure loss to above 180 Pa, an oil leakage warning signal is emitted. In the case of a relatively slow increase of pressure loss to above 170 Pa, a warning signal is emitted to indicate that the screen is clogged. A fan failure warning is emitted in the case of a pressure loss less than 100 Pa.

Alternatively, the difference between a clogged screen and the presence of an oil leakage may be determined in embodiments, in which the sensor and control system are adapted to monitor the pressure loss over time, i.e. continuously, and wherein the control system is configured to output at least one of:

the warning signal if the pressure loss exceeds said first predetermined threshold value; and an error signal if the pressure loss exceeds a second predetermined threshold level for a predetermined period of time.

The second predetermined threshold level is preferably smaller than the first predetermined threshold level. Hence, a relatively low pressure drop exceeding the second threshold level does not produce the warning signal indicative of an oil leakage. However, if the pressure drop exceeds the second threshold level for some time, this indicates that the screen is clogged by contamination other than contamination deriving from an oil leakage.

For example, a pressure loss of more than 150 Pa in more than 2 minutes results in the generation of the error signal. In preferred embodiments, a pressure loss of more than 200 Pa in 5-80 minutes, results in the generation of the error signal.

In a preferred embodiment, a warning signal indicative of an oil leakage is provided at a pressure loss of 225 Pa.

Preferred embodiments of the invention also provide a fan error signal, if the pressure loss across the screen is below a third threshold value, e.g. 80-120 Pa, such as 100 Pa.

The screen may form a plurality of openings for the airflow, the screen being made from e.g. a wire mesh. For reliable oil particle detection, the centre distance between neighbouring openings (equal to the centre distance between neighbouring wires) may be in the range of 10-100 µm, such as 30-80 µm, such as 40-80 µm. In one embodiment, a centre distance of approximately 73 µm has been applied. The diameter of the meshes of the screen may be in the range of 5-50 µm, such as 10-30 µm, such as approximately 20 µm.

The present invention also provides a vessel comprising an engine room and an oil leakage detector as disclosed herein. The oil leakage detector may be arranged in the engine room for efficient and reliable oil detection.

It will be appreciated that the invention further provides a method of detecting oil leakage, in particular in ambient air of an engine room of a vessel, comprising the steps of:

providing an airflow therethrough through a conduit, there being provided a screen in the conduit, the screen being meshed to at least partially prevent oil particles or droplets from passing therethrough;

determining a pressure loss across the screen;

outputting a warning signal if the pressure loss exceeds a first predetermined threshold value.

The step of determining the pressure loss across the screen may comprise a continuous monitoring of the pressure loss, and the step of outputting the warning signal may comprise at least one of:

outputting said warning signal if the pressure loss exceeds said first predetermined threshold value; and outputting an error signal if the pressure loss exceeds a second predetermined threshold level for a predetermined period of time.

BRIEF DESCRIPTION OF THE DRAWINGS

Embodiments of the present invention will now be described with reference to the accompanying drawings, in which.

DETAILED DESCRIPTION OF THE DRAWINGS

Figure 1:
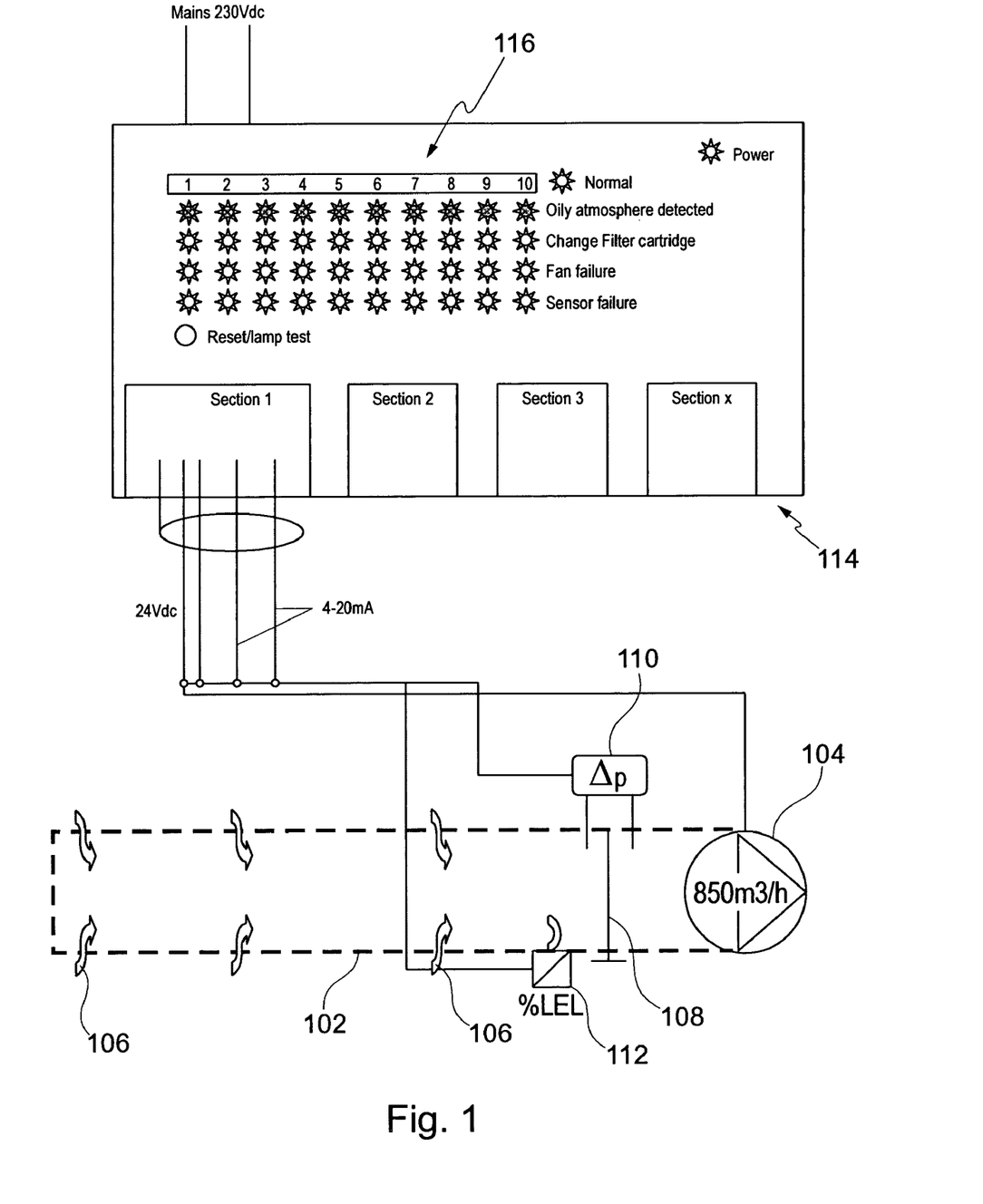
FIG. 1 is an illustration of a first embodiment of an oil leakage detector according to the present invention.

The oil leakage detector illustrated in FIG. 1 comprises a perforated conduit 102. At a downstream end of the conduit 102 there is provided a fan 104 for generating an airflow through the conduit. As illustrated by arrows 106, the fan draws air from the surrounding atmosphere, e.g. the engine room of a vessel, through the conduit. A screen 108 is provided upstream of the fan 104, but yet at a downstream location in the conduit 102. A pressure sensor is provided for determining the pressure loss across the screen 108, and a gas sensor 112 is optionally included in the vicinity of the screen 108. The pressure sensor 110, fan 104 and gas sensor 112 are connected to a control system 114 including a display panel 116 with warning lamps for emitting warning signals as described in the above summary of the invention. It will be appreciated that the control system 114 may be connected to a plurality of oil leakage sensors and/or to other surveillance equipment.

Figure 2:
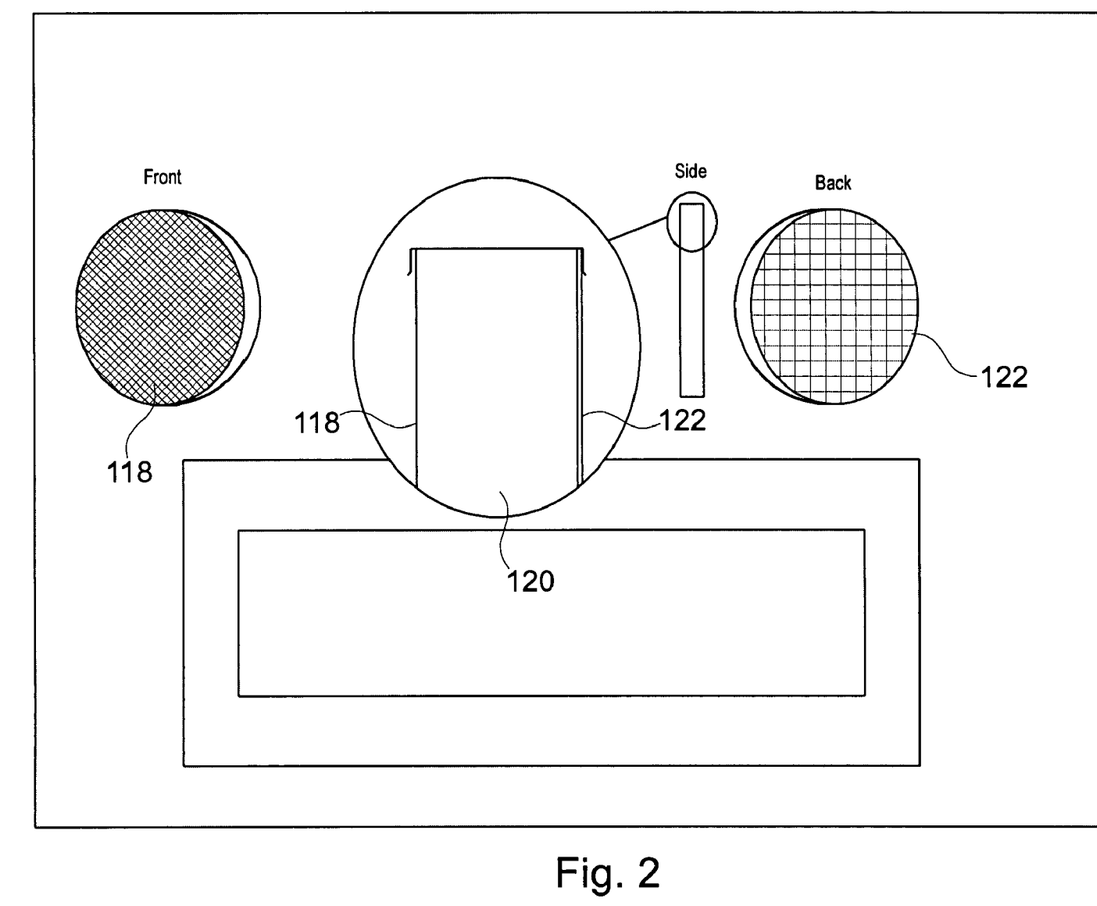
FIG. 2 is an illustration of a screen of the oil leakage detector of FIG. 1.

The screen 108 of the oil leakage detector is shown in more detail in FIG. 2. A front of the screen includes an oil droplet filter 118 in the form of a wire mesh (cf. FIG. 3). The oil droplet filter 118 is supported by a support structure 120. The support structure 120 should be open but yet stable. For example, the support structure may include a honeycomb structure of e.g. aluminium or siliconized paper. A further support 122 is provided at the back of the support structure, such as e.g. a coarse wire mesh of steel.

Figure 3:
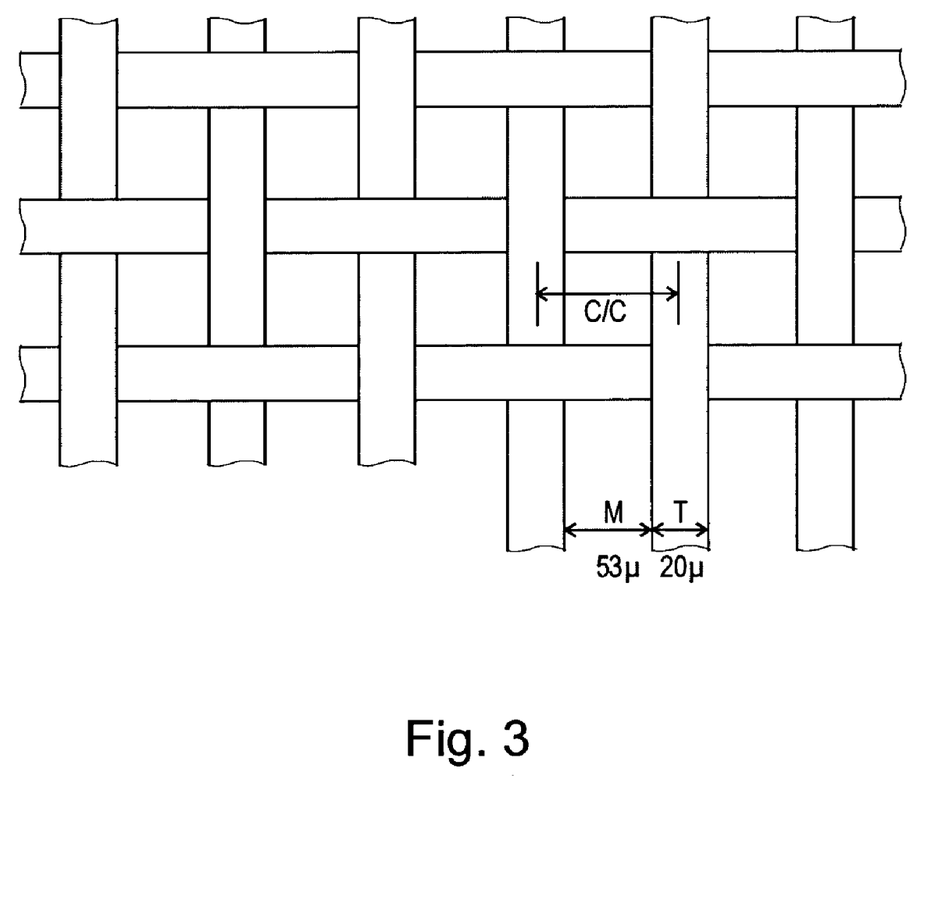
FIG. 3 is a sketch of a wire mesh of the screen of FIG. 2.

FIG. 3 includes a sketch of the wire mesh 118. The centre distance between neighbouring openings is denoted C/C and may be in the range of 10-100 µm, such as 30-80 µm, such as 40-80 µm, such as approximately 70 µm. In one embodiment, a centre distance of approximately 73 µm has been applied. The diameter of the meshes of the screen is denoted T and may be in the range of 5-50 µm, such as 10-30 µm, such as approximately 20 µm. The size of the meshes is denoted M. In the embodiment shown, the diameter T of the meshes of the screen is approximately 20 µm, the centre distance C/C is approximately 73 µm, and the size of the meshes M is approximately 53 µm.

Figure 4:
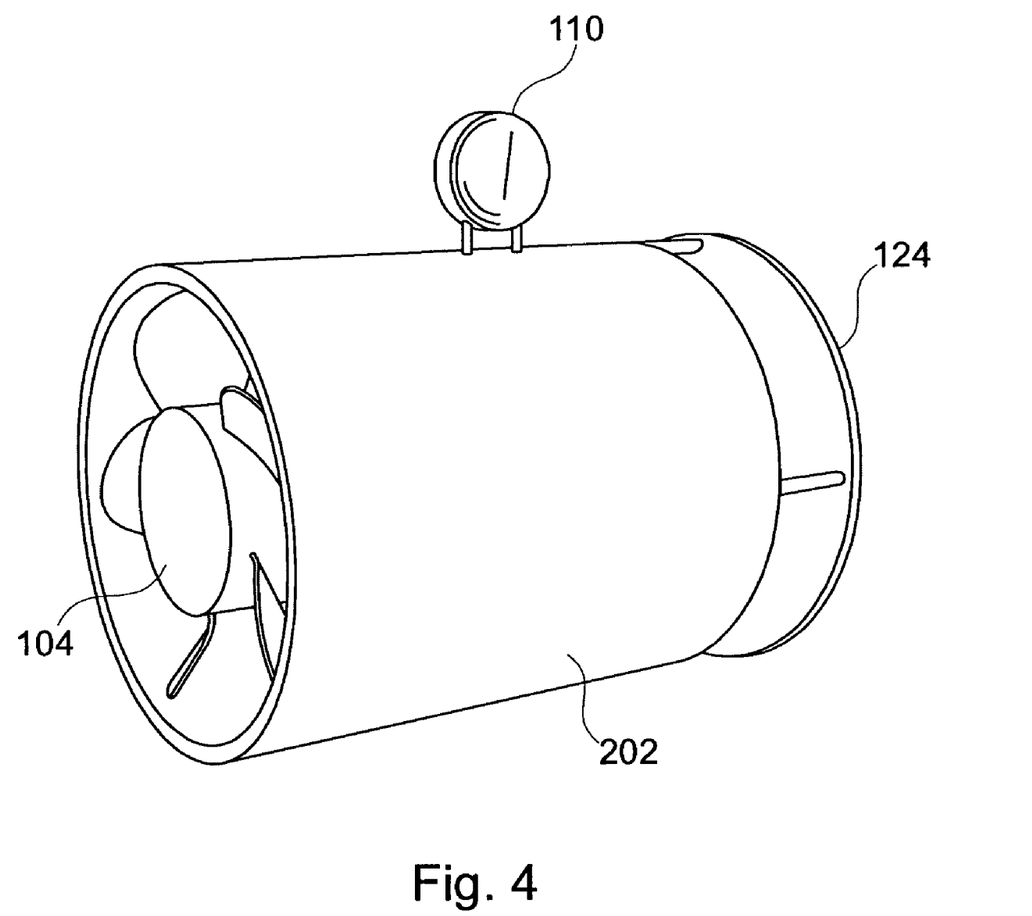
FIGS. 4-6 illustrate a second embodiment of an oil leakage detector according to the present invention.
Figure 5:
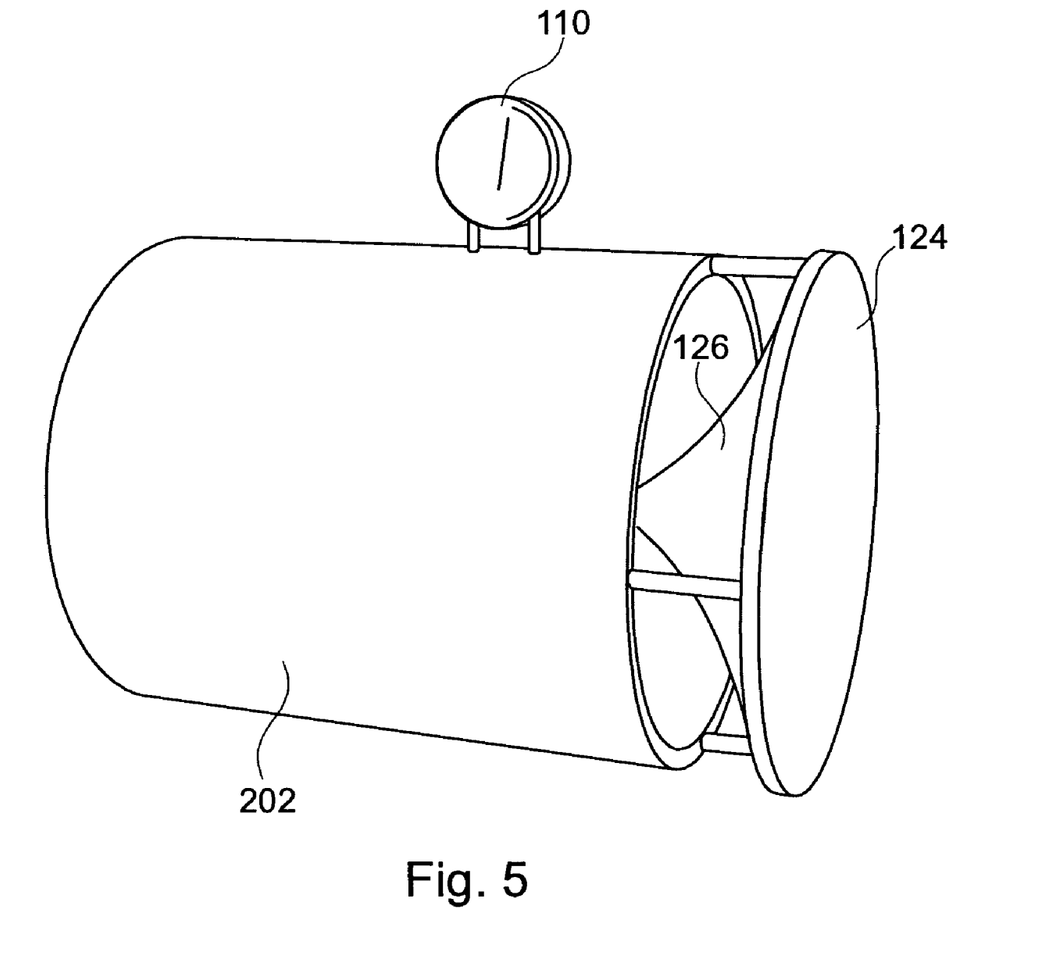
Figure 6:
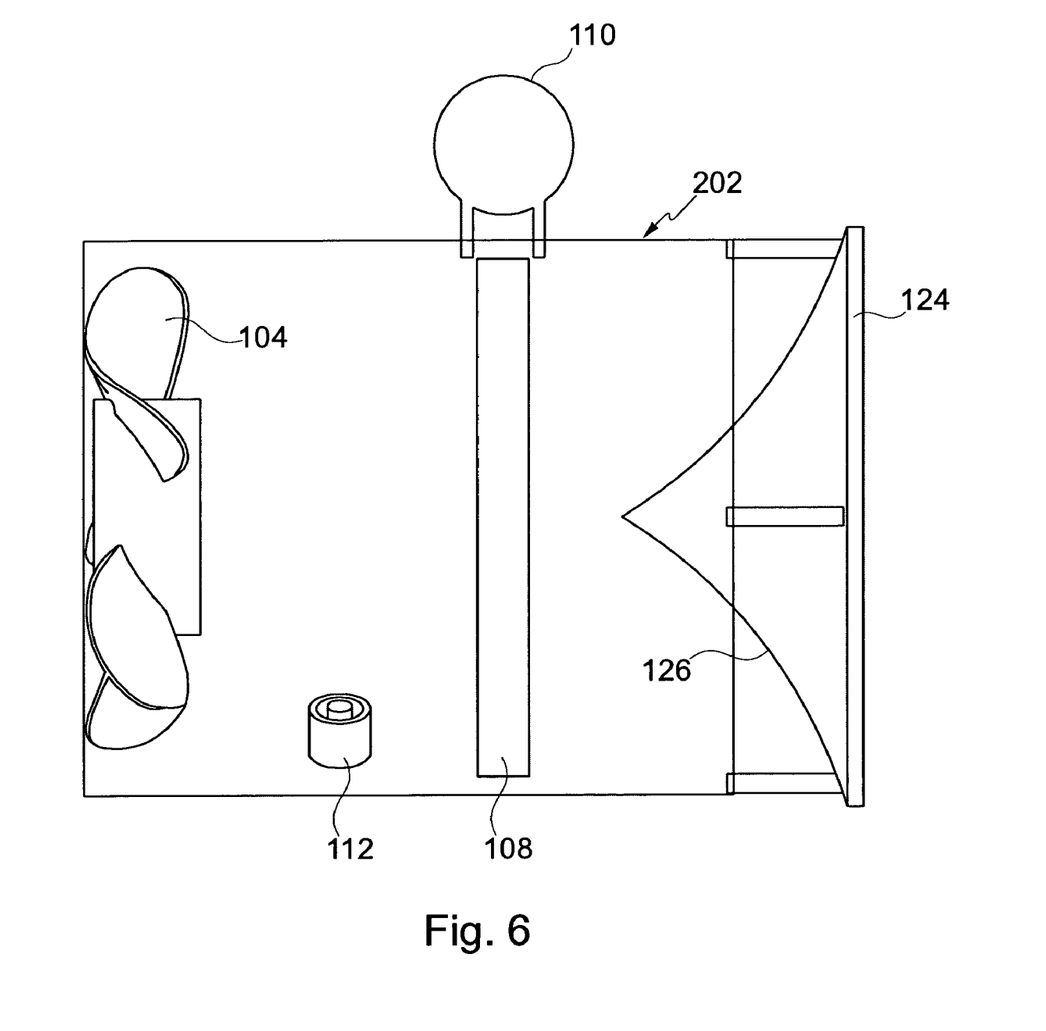

FIGS. 4-6 illustrate a second embodiment of an oil leakage detector according to the present invention. As shown in the cross-sectional view of FIG. 6, the detector comprises a non-perforated conduit 202 with an end member 124 at its inlet end, the end member being spaced from an end of the conduit 202 to provide a lateral inlet opening to the conduit. The end member 124 forms a cone-like member 126 for guiding a flow of air into the conduit 202. The conduit 202 accommodates screen 108, pressure sensor 110, gas sensor 112, and fan 104 at the downstream end, i.e. outlet end, of the conduit 202. The end member 124 may house control electronics receiving electrical output signals of the pressure sensor 110 and gas sensor 112 and possibly other control equipment. Likewise, warning signal emitters may be included in the end member 124.

FIG. 4 shows a perspective illustration seen from the downstream, i.e. outlet end, of the conduit 202, and FIG. 5 shows a perspective illustration seen from the upstream, i.e. inlet end, of the conduit 202.

The invention claimed is:

1. An oil leakage detector, comprising:
a conduit for an airflow therethrough;

a screen in the conduit, the screen being meshed to at least partially prevent oil particles or droplets from passing therethrough;

a sensor for determining a pressure loss across the screen;

a control system operatively connected to the sensor, the control system being configured to output a warning signal if the pressure loss exceeds a predetermined threshold value;

wherein the sensor and the control system are arranged to continuously monitor said pressure loss, the control system being further configured to output an error signal if the pressure loss exceeds a second predetermined threshold level, which is lower than said first predetermined threshold level;

characterised in that the control system is configured to output the error signal only if the pressure loss exceeds the second predetermined threshold level for a predetermined period of time.

2. An oil leakage detector according to claim 1, further comprising a fan for providing said airflow through the conduit.

3. An oil leakage detector according to claim 1, wherein the screen is arranged at a downstream location in the conduit.

4. An oil leakage detector according to claim 1, further comprising a gas sensor for determining the presence of at least one gas in the airflow in the conduit.

5. An oil leakage detector according to claim 4, wherein the control system is connected to the gas sensor.

6. An oil leakage detector according to claim 5, wherein the control system is configured to emit an error signal and/or said warning signal in one or more of the following events:

the pressure loss exceeds a predetermined threshold value due to oily atmosphere;

fan failure;

clogged screen;

gas sensor failure.

7. An oil leakage detector according to claim 1, wherein the screen forms a plurality of openings for the airflow, and wherein the centre distance between neighbouring openings is 10-100 μm.

8. An oil leakage detector according to claim 1, wherein the screen is essentially made from meshes with a diameter of 5-50 μm.

9. An oil leakage detector according to claim 2, wherein the fan is arranged at a downstream location in the conduit.

10. A vessel comprising an engine room and an oil leakage detector according to claim 1.

11. A method of detecting oil leakage, comprising the steps of:

providing an airflow therethrough through a conduit, there being provided a screen in the conduit, the screen being meshed to at least partially prevent oil particles or droplets from passing therethrough;

determining a pressure loss across the screen by continuously monitoring the pressure loss;

outputting a warning signal if the pressure loss exceeds a first predetermined threshold value; and outputting an error signal if the pressure loss exceeds a second predetermined threshold level, which is lower than said first predetermined threshold level, only if the pressure loss exceeds the second level for a predetermined period of time.

* * * * *